US00PP33335P2

(12) United States Plant Patent
Verschoor

(10) Patent No.: US PP33,335 P2
(45) Date of Patent: Aug. 10, 2021

(54) ***PHLOX* PLANT NAMED 'VERSLUCK'**

(50) Latin Name: *Phlox paniculata*
Varietal Denomination: Versluck

(71) Applicant: Janus Verschoor, Haarlem (NL)

(72) Inventor: Janus Verschoor, Haarlem (NL)

(73) Assignee: A. VERSCHOOR HORTICULTURE IMPORT-EXPORT B.V., Haarlem (NL)

( * ) Notice: Subject to any disclaimer, the term of this patent is extended or adjusted under 35 U.S.C. 154(b) by 0 days.

(21) Appl. No.: 17/083,752

(22) Filed: Oct. 29, 2020

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 6/70
See application file for complete search history.

*Primary Examiner* — Anne Marie Grunberg
(74) *Attorney, Agent, or Firm* — Penny J. Aguirre

(57) ABSTRACT

A new cultivar of *Phlox* plant named 'Versluck' that is characterized by its dwarf plant habit, its re-blooming habit, its flowers that are a blend of white and violet-purple on color with an eye that is dark pink in color, its strong basal branching, and its partial resistance to powdery mildew.

2 Drawing Sheets

Botanical classification: *Phlox paniculata.*
Cultivar designation: 'Versluck'.

CROSS REFERENCE TO RELATED APPLICATIONS

This application is related to U.S. Plant Patents for plants derived from the same breeding program that is entitled *Phlox* Plant Named 'Verscan' (U.S. Plant Pat. No. 27,558) and *Phlox* Plant Named 'Versde' (U.S. Plant Pat. No. 27,557).

BACKGROUND OF THE INVENTION

The present invention relates to a new and distinct cultivar of *Phlox paniculata* and will be referred to hereafter by its cultivar name, 'Versluck'. 'Versluck' represents a new herbaceous perennial grown for landscape use.

'Versluck' was discovered by the Inventor as a chance seedling in a trial field in Haarlem, The Netherlands in 2014. The parentage is unknown.

Asexual propagation of the new cultivar was first accomplished by stem cuttings by the Inventor in 2015 in Haarlem, The Netherlands. Asexual propagation by stem cuttings, root cuttings, and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Versluck' as a unique cultivar of *Phlox*.

1. 'Versluck' exhibits a very dwarf plant habit.
2. 'Versluck' exhibits a re-blooming habit.
3. 'Versluck' exhibits flowers that are a blend of white and violet-purple on color with an eye that is dark pink in color.

4. 'Versluck' exhibits strong basal branching.
5. 'Versluck' exhibits some resistance to powdery mildew.

'Versluck' can be compared to *Phlox paniculata* cultivars 'Verscan' and 'Versde'. Both are similar to 'Versluck' in having very compact plant habits. 'Verscan' differs from 'Versluck' in having bi-color flowers that are red-purple and white in color. 'Versde' differs from 'Versluck' in having flowers that are pink in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Growing Colors, Soegel Home and Garden, Diane's Greenhouse, and Vite Greenhouses.

BRIEF DESCRIPTION OF THE DRAWINGS

The accompanying colored photographs illustrate the overall appearance and distinct characteristics of the new *Phlox*. The photographs were taken of a 2-year-old plant of 'Versluck' as grown in a 23-cm container Haarlem, The Netherlands.

The photograph in FIG. 1 is a view of a plant of 'Versluck' in bloom.

Figure 1:
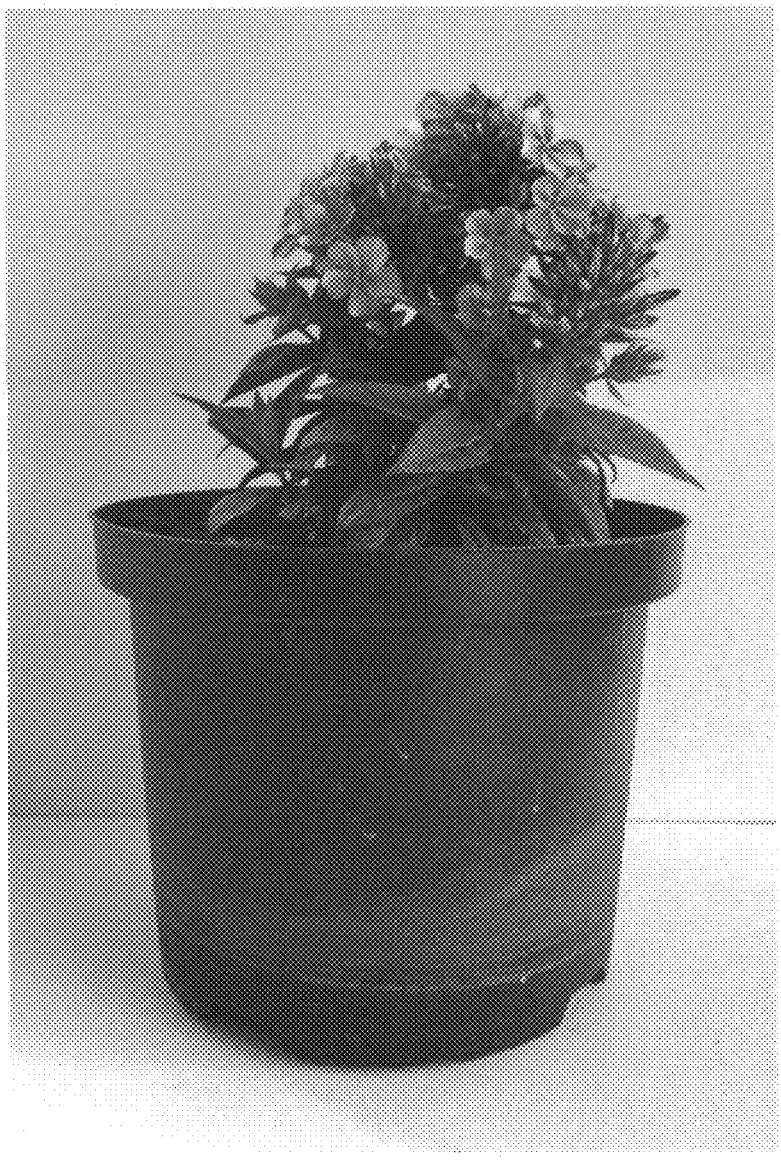
Figure 2:
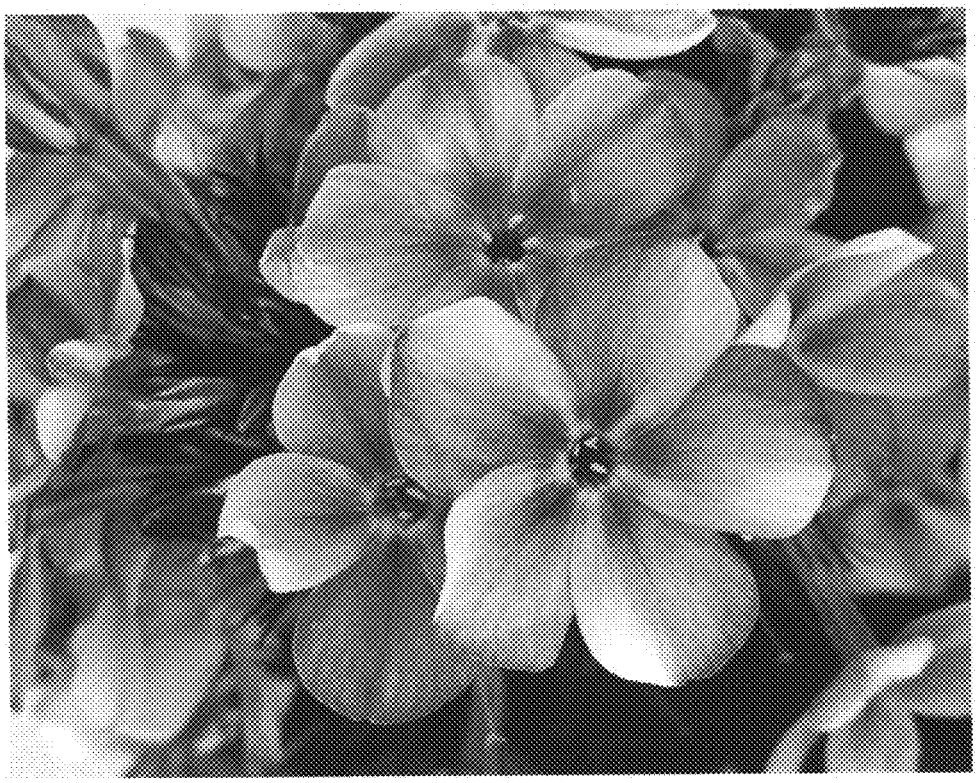

The photograph in FIG. 2 is a close-up view of the flowers of 'Versluck'.

Figure 3:
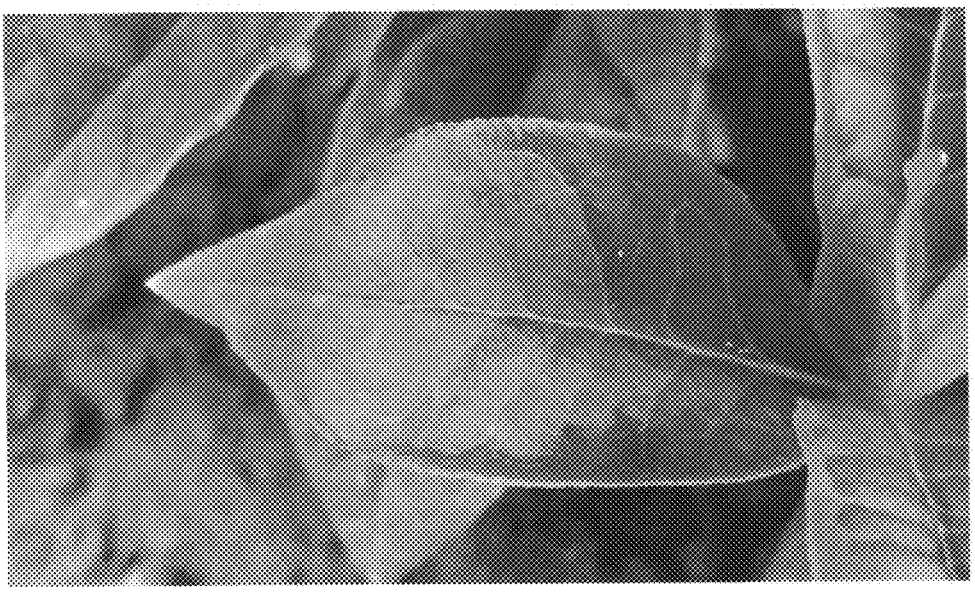

The photograph in FIG. 3 provides a close-up view of the foliage of 'Versluck'.

The colors in the photographs may differ slightly from the color values cited in the detailed botanical description, which accurately describe the colors of the new *Phlox*.

DETAILED BOTANICAL DESCRIPTION OF THE PLANT

The following is a detailed description of 2-year-old plants of the new cultivar as grown in 23-cm containers in Haarlem, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Early July to September in The Netherlands, re-blooming.

*Plant type*.—Herbaceous perennial.

*Plant habit*.—Very dwarf, compact.

*Height and spread*.—Average of 19.5 cm in height, 21 cm in width.

*Hardiness*.—At least in U.S.D.A. Zones 4 to 9.

*Diseases and pests*.—Some resistance to powdery mildew caused by *Erysiphe cichoracearum* has been observed when grown under the same conditions with other cultivars that lacked resistance.

*Root description*.—Fibrous.

*Growth rate*.—Moderately vigorous.

*Propagation*.—Stem cuttings, root cuttings and tissue culture.

*Root initiation*.—About 30 days in summer.

*Root development*.—Average of 28 weeks from a rooted cutting to fully develop in a 1.5-liter container.

Stem description:

*Stem quantity*.—Average of 3 flowering stems.

*Stem size*.—13 cm in length, 3.5 mm in diameter.

*Stem shape*.—Round.

*Stem strength*.—Strong.

*Stem color*.—144B.

*Stem surface*.—Glabrous and moderately glossy.

*Stem aspect*.—Held in an average angle of 45° (varying between 40° and 60°).

*Internode length*.—An average of 1.5 cm.

*Branching habit*.—Freely branching, main stems grow from the base.

Foliage description:

*Leaf shape*.—Narrowly ovate to elliptic.

*Leaf division*.—Simple.

*Leaf base*.—Truncate.

*Leaf apex*.—Apiculate.

*Leaf venation*.—Pinnate, color upper side 144A, color lower side 144B.

*Leaf margins*.—Entire, but very finely serrate.

*Leaf attachment*.—Petiolate.

*Leaf arrangement*.—Opposite.

*Leaf surface*.—Both surfaces are very slightly rugose, upper side very slightly glossy, lower side matte.

*Leaf color*.—Young upper surface; 143A, young lower surface; 143B, mature upper surface; NN137A, mature lower surface; 147B.

*Leaf size*.—An average of 6 cm in length and 2.7 cm in width.

*Leaf quantity*.—An average of 18 (9 pairs) per stem.

*Petioles*.—V-shaped, an average of 2.5 mm in height, 4 mm in width, 144B in color, both surfaces are glabrous.

Flower description:

*Inflorescence type*.—Compound terminal panicle.

*Lastingness of inflorescence*.—Freely flowering, individual flowers lasts about 10 days, 3 to 4 weeks per inflorescence, inflorescences are continuously produced during the bloom season.

*Inflorescence size*.—An average of 9 cm in height and width.

*Flower fragrance*.—Moderate, sweet and pleasant *Phlox* fragrance.

*Flower number*.—Average of 90 per inflorescence.

*Flower aspect*.—Upright to outward.

*Flower bud*.—An average of 1.8 cm in length and up to 4 mm in diameter, narrow obovate in shape, smooth and glabrous texture, very slightly glossy, color; 155C, top 90B, immature tube 145B, immature calyx 145A, tinged 187A.

*Flower form*.—Explanate with tubular base.

*Flower size*.—An average of 3 cm in diameter, 2.4 cm in depth.

*Petals*.—5, rotate and overlapping, self-cleaning, both surfaces are glabrous, surfaces are glabrous, upper surface matte, lower surface slightly glossy, petals are fused 65% into tube, spathulate in shape, margins entire, obtuse to slightly retuse apex, average of 3 cm in length, 1.7 cm in width, color: when opening upper surface; 93B and 155D, tube 145B to 145C, when opening lower surface; 88C with 155D, fully open upper side; N82B and N87A fading to 155D, N81B towards throat (eye zone), tube N87A and 155D, fully open lower side; N82B, fading to 155D, tube N87A and 155D.

*Sepals*.—5, 15% of base fused, rotate, linear in shape, margins entire, apex narrowly apiculate in shape, an average of 1 cm in length and 1 mm in width, both surfaces are glabrous and very slightly glossy, color: immature upper surface; 144A, main vein and margins tinged N187A, immature lower surface; 145A, main vein and margins tinged N187A, mature upper surface; 144A, main vein and margins tinged N187A, mature lower surface; 145A, main vein and margins tinged N187A.

*Peduncles*.—Strong, oval in shape, strong, 6 cm in length, 3 mm in diameter, held in an angle of 45°, smooth, glabrous and moderately glossy surface, 144A in color.

Pedicels.—Strong, oval in shape, strong, 5 cm in length, 1 mm in diameter, held in an angle of 45°, smooth, glabrous and moderately glossy surface, 145A in color.

Reproductive organs:

*Gynoecium*.—Pistil; 1, 1.7 cm in length, stigma; cleft (3-parted), 150D in color, 1.6 mm in length, style; 1.6 cm in length, 149D in color, ovary; 143A in color.

*Androecium*.—Stamens; 5, anthers; basifixed and oblong in shape, 2 mm in length, 160D in color, filaments; 0.5 mm in length, 160D in color, pollen is low in quantity and 155A in color.

*Seeds*.—None observed to date.

It is claimed:

1. A new and distinct cultivar of *Phlox* plant named 'Versluck' as herein illustrated and described.

* * * * *